(12) United States Patent
Linares et al.

(10) Patent No.: US 8,702,802 B2
(45) Date of Patent: Apr. 22, 2014

(54) KNEE IMPLANT ASSEMBLY WITH ROTARY BEARING SUPPORTED AND TRAVELING SURFACES

(75) Inventors: Miguel A. Linares, Bloomfield Hills, MI (US); Miguel A. Linares, Jr., Bloomfield Hills, MI (US)

(73) Assignee: Linares Medical Devices, LLC, Auburn Hills, MI (US)

(*) Notice: Subject to any disclaimer, the term of this patent is extended or adjusted under 35 U.S.C. 154(b) by 0 days.

(21) Appl. No.: 13/597,313

(22) Filed: Aug. 29, 2012

(65) Prior Publication Data
US 2013/0053978 A1 Feb. 28, 2013

Related U.S. Application Data

(60) Provisional application No. 61/528,300, filed on Aug. 29, 2011.

(51) Int. Cl.
*A61F 2/38* (2006.01)

(52) U.S. Cl.
USPC .................................. 623/20.21; 623/23.39

(58) Field of Classification Search
CPC ....................................................... A61F 2/38
USPC ................................ 623/18.11, 20.11, 20.14
See application file for complete search history.

(56) References Cited

U.S. PATENT DOCUMENTS

| | | | |
|---|---|---|---|
| 1,051,444 A | 1/1913 | Pleister | |
| 2,314,445 A | 3/1943 | DuVall | |
| 2,667,644 A | 2/1954 | Johnson | |
| 2,821,979 A | 2/1958 | Cameron | |
| 3,694,820 A | 10/1972 | Scales et al. | |
| 3,815,157 A | 6/1974 | Skorecki et al. | |
| 3,973,277 A | 8/1976 | Semple et al. | |
| 4,040,131 A | 8/1977 | Gristina | |
| 4,045,825 A | 9/1977 | Stroot | |
| 4,483,023 A | 11/1984 | Hoffman, Jr. et al. | |

(Continued)

FOREIGN PATENT DOCUMENTS

| | | |
|---|---|---|
| EP | 1228739 A2 | 8/2002 |
| WO | 9800076 A1 | 1/1998 |
| WO | 2004080331 A2 | 9/2004 |
| WO | 2009039164 A1 | 3/2009 |

OTHER PUBLICATIONS

Tan et al., "Developments of an Antimicrobial Microporous Polyurethane Membrane", Journal of Membrane Science, 289. 199-209 (2007).

*Primary Examiner* — Jason-Dennis Stewart
(74) *Attorney, Agent, or Firm* — Gifford, Krass, Sprinkle, Anderson & Citkowski, P.C.; Douglas J. McEvoy

(57) ABSTRACT

A joint assembly incorporated into a reconditioned end surface established between upper and opposing lower bones. At least one first component is anchored into a first of the reconditioned bone end surfaces and exhibits a rotatably supported wheel. A second component is anchored into a second opposing reconditioned bone end surfaces and exhibits a second exposed support surface in contact with the rotatably supported wheel. The first component includes a supporting well anchored into the reconditioned bone end surface for supporting the wheel in rotatable fashion. A laterally inserting pin displaces relative to a side of the wheel well and into an interior thereof and includes a central axial through hole which receives the pin for supporting the shaft.

7 Claims, 6 Drawing Sheets

(56) References Cited

U.S. PATENT DOCUMENTS

| | | | |
|---|---|---|---|
| 4,501,031 | A | 2/1985 | McDaniel et al. |
| 4,665,951 | A | 5/1987 | Ellis |
| 4,693,723 | A | 9/1987 | Gabard |
| 4,744,793 | A | 5/1988 | Parr et al. |
| 4,778,473 | A | 10/1988 | Matthews et al. |
| 4,792,336 | A | 12/1988 | Hlavacek et al. |
| 4,828,562 | A | 5/1989 | Kenna |
| 4,840,630 | A | 6/1989 | Kitamura |
| 4,851,005 | A | 7/1989 | Hunt et al. |
| 4,883,486 | A | 11/1989 | Kapadia et al. |
| 4,906,149 | A | 3/1990 | Rockenfeller et al. |
| 5,004,474 | A | 4/1991 | Fronk et al. |
| 5,078,745 | A | 1/1992 | Rhenter et al. |
| 5,171,325 | A | 12/1992 | Aulie |
| 5,263,984 | A | 11/1993 | Li et al. |
| 5,282,867 | A | 2/1994 | Mikhail |
| 5,376,119 | A | 12/1994 | Zimmermann et al. |
| 5,389,107 | A | 2/1995 | Nassar et al. |
| 5,417,693 | A | 5/1995 | Sowden et al. |
| 5,443,516 | A * | 8/1995 | Albrektsson et al. ...... 623/23.39 |
| 5,462,563 | A | 10/1995 | Shearer et al. |
| 5,486,197 | A | 1/1996 | Le et al. |
| 5,507,819 | A | 4/1996 | Wolf |
| 5,554,194 | A | 9/1996 | Sanders |
| 5,571,191 | A | 11/1996 | Fitz |
| 5,575,819 | A | 11/1996 | Amis et al. |
| 5,593,448 | A | 1/1997 | Dong |
| 5,609,647 | A | 3/1997 | Kalberer et al. |
| 5,676,702 | A | 10/1997 | Ratron et al. |
| 5,702,469 | A | 12/1997 | Whipple et al. |
| 5,702,486 | A | 12/1997 | Craig et al. |
| 5,707,395 | A | 1/1998 | Li |
| 5,723,018 | A | 3/1998 | Cyprien et al. |
| 5,728,175 | A | 3/1998 | Rincoe |
| 5,741,335 | A | 4/1998 | Gerber et al. |
| 5,800,566 | A | 9/1998 | Gramnas et al. |
| 5,879,404 | A | 3/1999 | Bateman et al. |
| 5,921,358 | A | 7/1999 | Gramnas et al. |
| 5,961,555 | A | 10/1999 | Huebner |
| 6,001,106 | A | 12/1999 | Ryan et al. |
| 6,010,535 | A | 1/2000 | Shah |
| 6,190,411 | B1 | 2/2001 | Lo et al. |
| 6,193,758 | B1 | 2/2001 | Huebner |
| 6,197,063 | B1 | 3/2001 | Dews |
| 6,245,109 | B1 | 6/2001 | Mendes et al. |
| 6,325,804 | B1 | 12/2001 | Wenstrom, Jr. et al. |
| 6,383,223 | B1 | 5/2002 | Baehler et al. |
| 6,582,715 | B1 | 6/2003 | Barry et al. |
| 6,620,197 | B2 | 9/2003 | Maroney et al. |
| 6,626,942 | B1 | 9/2003 | Edberg et al. |
| 6,645,251 | B2 | 11/2003 | Salehi et al. |
| 6,776,799 | B2 | 8/2004 | Ball et al. |
| 6,790,234 | B1 | 9/2004 | Frankle |
| 6,840,962 | B1 | 1/2005 | Vacanti et al. |
| 6,939,379 | B2 | 9/2005 | Sklar |
| 6,986,790 | B2 | 1/2006 | Ball et al. |
| 7,033,396 | B2 | 4/2006 | Tornier |
| 7,044,983 | B1 | 5/2006 | Cheng et al. |
| 7,056,340 | B2 | 6/2006 | McKernan et al. |
| 7,066,958 | B2 | 6/2006 | Ferree |
| 7,087,091 | B1 | 8/2006 | Chen et al. |
| 7,097,663 | B1 | 8/2006 | Nicol et al. |
| 7,101,398 | B2 | 9/2006 | Dooris et al. |
| 7,153,327 | B1 | 12/2006 | Metzger |
| 7,169,184 | B2 | 1/2007 | Dalla Pria |
| 7,175,663 | B1 | 2/2007 | Stone |
| 7,175,666 | B2 | 2/2007 | Yao |
| 7,189,261 | B2 | 3/2007 | Dews et al. |
| 7,309,360 | B2 | 12/2007 | Tornier et al. |
| 7,329,281 | B2 | 2/2008 | Hays et al. |
| 7,331,995 | B2 | 2/2008 | Eisermann et al. |
| 7,445,638 | B2 | 11/2008 | Beguin et al. |
| 7,462,197 | B2 | 12/2008 | Tornier et al. |
| 7,465,319 | B2 | 12/2008 | Tornier |
| 7,510,558 | B2 | 3/2009 | Tallarida et al. |
| 7,708,781 | B2 | 5/2010 | Scheker |
| 2001/0051831 | A1 | 12/2001 | Subba Rao et al. |
| 2002/0013627 | A1 | 1/2002 | Geistlich et al. |
| 2002/0143402 | A1 | 10/2002 | Steinberg |
| 2003/0130741 | A1 | 7/2003 | McMinn |
| 2004/0024460 | A1 | 2/2004 | Ferree |
| 2004/0064187 | A1 | 4/2004 | Ball et al. |
| 2004/0064188 | A1 | 4/2004 | Ball et al. |
| 2004/0068322 | A1* | 4/2004 | Ferree ...................... 623/23.39 |
| 2004/0210317 | A1 | 10/2004 | Maroney et al. |
| 2004/0225370 | A1 | 11/2004 | Cruchet et al. |
| 2004/0267370 | A1 | 12/2004 | Ondrla |
| 2005/0081867 | A1 | 4/2005 | Murphy |
| 2005/0187620 | A1 | 8/2005 | Pai et al. |
| 2005/0192674 | A1 | 9/2005 | Ferree |
| 2005/0261775 | A1 | 11/2005 | Baum et al. |
| 2005/0278032 | A1 | 12/2005 | Tornier et al. |
| 2006/0058886 | A1 | 3/2006 | Wozencroft |
| 2006/0074423 | A1 | 4/2006 | Alleyne et al. |
| 2006/0111787 | A1 | 5/2006 | Bailie et al. |
| 2006/0149370 | A1 | 7/2006 | Schmieding et al. |
| 2007/0005074 | A1 | 1/2007 | Chudik |
| 2007/0005137 | A1 | 1/2007 | Kwak |
| 2007/0088442 | A1 | 4/2007 | Cima et al. |
| 2008/0234830 | A1 | 9/2008 | Hershberger et al. |
| 2009/0039164 | A1 | 2/2009 | Herwig et al. |
| 2009/0088865 | A1 | 4/2009 | Brehm |
| 2009/0292364 | A1 | 11/2009 | Linares |
| 2011/0004316 | A1* | 1/2011 | Murray et al. ............... 623/20.3 |

\* cited by examiner

US 8,702,802 B2

KNEE IMPLANT ASSEMBLY WITH ROTARY BEARING SUPPORTED AND TRAVELING SURFACES

CROSS REFERENCE TO RELATED APPLICATIONS

The present application claims priority of U.S. Ser. No. 61/528,300 filed Aug. 29, 2011.

BACKGROUND OF THE INVENTION

1. Field of the Invention

The present invention discloses an artificial joint assembly, such as is particularly configured for employing as a retrofit knee joint, and which combines upper and lower pairs of artificial components incorporated into first and second reconditioned joint defining surfaces for providing increased wear life in tandem with evenly distributed wear pattern/profile as well as enhanced flexibility and mobility.

2. Description of the Background Art

The prior art is well documented with examples of artificial knee implant assemblies. These include such as the spherical knee joint prosthesis of Bosredon, U.S. Pat. No. 6,117,175, the total knee implant of Byrd et al., US 2010/0191342 and the artificial implant component and method for securing disclosed in Elias, U.S. Pat. No. 5,480,443.

SUMMARY OF THE PRESENT INVENTION

The present invention discloses a joint assembly incorporated into a reconditioned end surface established between upper and opposing lower bones. The assembly includes a first component anchored into a first of the reconditioned bone end surfaces and exhibiting a rotatably supported wheel and a second component anchored into a second of the reconditioned bone end surfaces and exhibiting a second exposed support surface in contact with the rotatably supported wheel.

Additional features include the first component further comprising a supporting well anchored into the reconditioned bone end surface for supporting the wheel in rotatable fashion. Each of the first and second components may further be constructed of at least one of a metal, plastic, polymer or composite material.

A first pair of components are arranged at a first side of said assembly between the upper and lower joint defining bones, with a second identical pair arranged at an opposite second side. In one application, a single pair of components define a ½ implant assembly associated with a selected side of the joint defining bones, such as associated with a partial implant configuration.

A laterally inserting and axially supporting pin displaces relative to a side of the wheel well and into an interior thereof. The wheel includes a central axial through hole which, upon pre-locating the wheel within the interior of the well, receives the pin an in an inserting direction, with an extending end of the pin seating within a journal end support defined on an opposing inner face of the well for supporting the shaft.

In this arrangement, a width dimension of the wheel is dimensioned slightly less than a corresponding inner width dimension of the well housing in order to facilitate a degree of lateral (side-to-side) motion of the wheel in combination with rotational motion. The well housings each further have additional and inner secured secondary width extending bearings mounted within journaled interior and circumferentially spaced locations, such that contacting outer annular surfaces of the wheels are supported within the well interior in order to further facilitate ease of rotation of the wheels.

The well housings may each further include a plural arrangement of substantially embedded and surface exposed eccentrically supporting ball bearings within circumferentially defined locations, such that contacting outer annular surfaces of the wheels are supported within the well interior in order to further facilitate rotation of the wheels. In a further variant, exposed support surface of the second component further exhibiting a slightly inwardly recessed profile for supporting an outer annular surfaces of the wheel, a reverse underside of the second component further including an integrally extending stem recess mounting within the second reconditioned bone end surface.

BRIEF DESCRIPTION OF THE DRAWINGS

Reference will now be made to the attached drawings, when read in combination with the following detailed description, wherein like reference numerals refer to like parts throughout the several views, and in which.

DETAILED DESCRIPTION OF THE PREFERRED EMBODIMENTS

As will be disclosed with succeeding reference to the several depicted embodiments, the present invention discloses an artificial joint assembly, such as is particularly configured for employing as a retrofit knee joint, and which combines upper and lower artificial components incorporated into first and second reconditioned joint defining surfaces for providing increased wear life in tandem with evenly distributed wear pattern/profile as well as enhanced flexibility and mobility.

The joint assemblies described herein are particularly configured for such as in situ reconditioned installation within a patient's knee assembly (between the lower end of the upper femur bone and corresponding upper end of the lower tibia bone), however it is further understood that certain applications could in theory include other joint applications, either human or other mammalian. For purposes of ease and clarify of illustration, the various embodiments depicted further do not include reference to additional necessary components of the knee joints, such as including the patella (knee cap) and associated muscles, tendons and ligaments, the inclusion of which are assumed and which collectively define a functioning knee joint.

Figure 1:
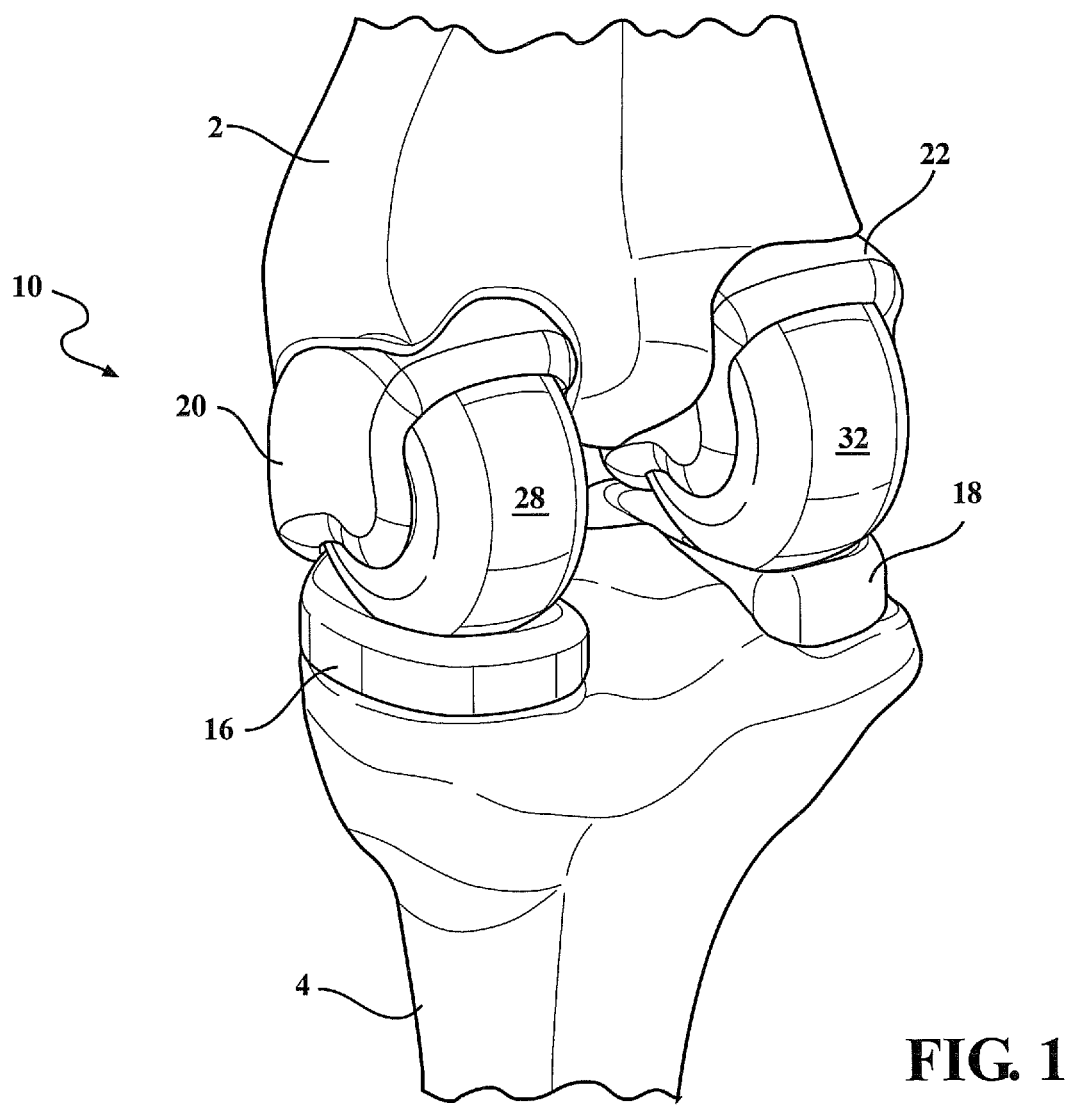
FIG. 1 is a perspective view of a knee implant assembly according to a first embodiment of the invention.

Referring now to FIG. 1, a perspective view is generally shown at 10 of a knee implant assembly according to a first embodiment of the invention and which is incorporated between an upper leg (femur) bone 2 and a lower leg (tibia) bone 4 (and with which an associated fibula bone is also not depicted). The present invention contemplates such as in situ reconditioning of the bone ends, illustrated by conditioned end profiles 6 configured into bottom most and generally oppositely facing end surface of the femur 2, as further depicted by a separating or bridging contoured surface 5.

Also shown are laterally defined and recessed profiles, also depicted as aligning apertures, and which are shown at 7 extending into opposite sides of the bridging surface 5 in communication with the contoured recess profiles 6. Opposing upper end facing and recesses 8 are also best illustrated in the exploded view of FIG. 2, these depicted as linear holes defined in the upper most end of tibia 4 as defined by flattened reconditioned profiles or ledges depicted at 11, with a separating or bridging location depicted at 9 defined between the recesses 8.

Such reconditioning prior to implantation is typically conducted in situ and occurs following incision or removal of any remaining damaged bone and/or cartilage associated with the damaged joint and during an appropriate surgical procedure utilizing medical drilling, boring and shaping instruments in order to recondition the joint defining bone ends and to create the desired shaping and profile of the joint. As previously indicated, it is advantageous to refashion the joint end profiles in situ during an appropriate surgical procedure, a further objective being to retain or repair, where possible, natural ligament, cartilage and muscle (not shown) associated with a normal functioning joint.

Figure 4:
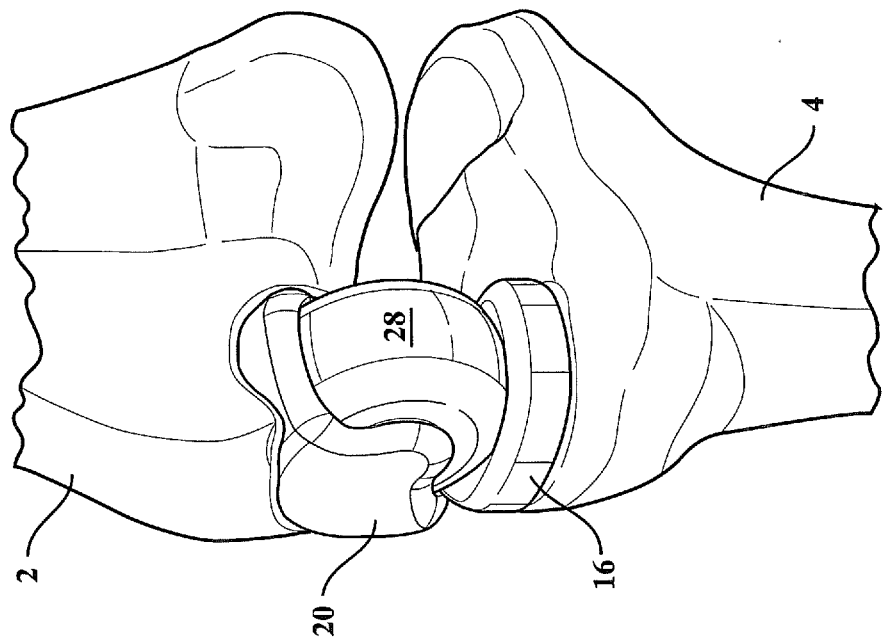
FIG. 4 is an illustration substantially identical to that previously depicted in FIG. 1 and presenting only a selected side or ½ implant assembly according to a further potential sub-variant.

Although not shown, such reconditioning can be employed with minimal interference to such necessary additional elements of the joint including each of the patella or knee cap, ligaments, muscles and tendons. Without limitation, it is further understood that the joint assemblies described in each of the illustrated variants can be integrated into either of human or synthetic bones (such as which can also contemplate both human and synthetic bones in a single joint application), with such joint assemblies also capable of surgically implanted in either total or partial (as depicted in FIG. 4) manner concurrent with any necessary degree of refashioning or removal of damaged bone or joint.

Figure 2:
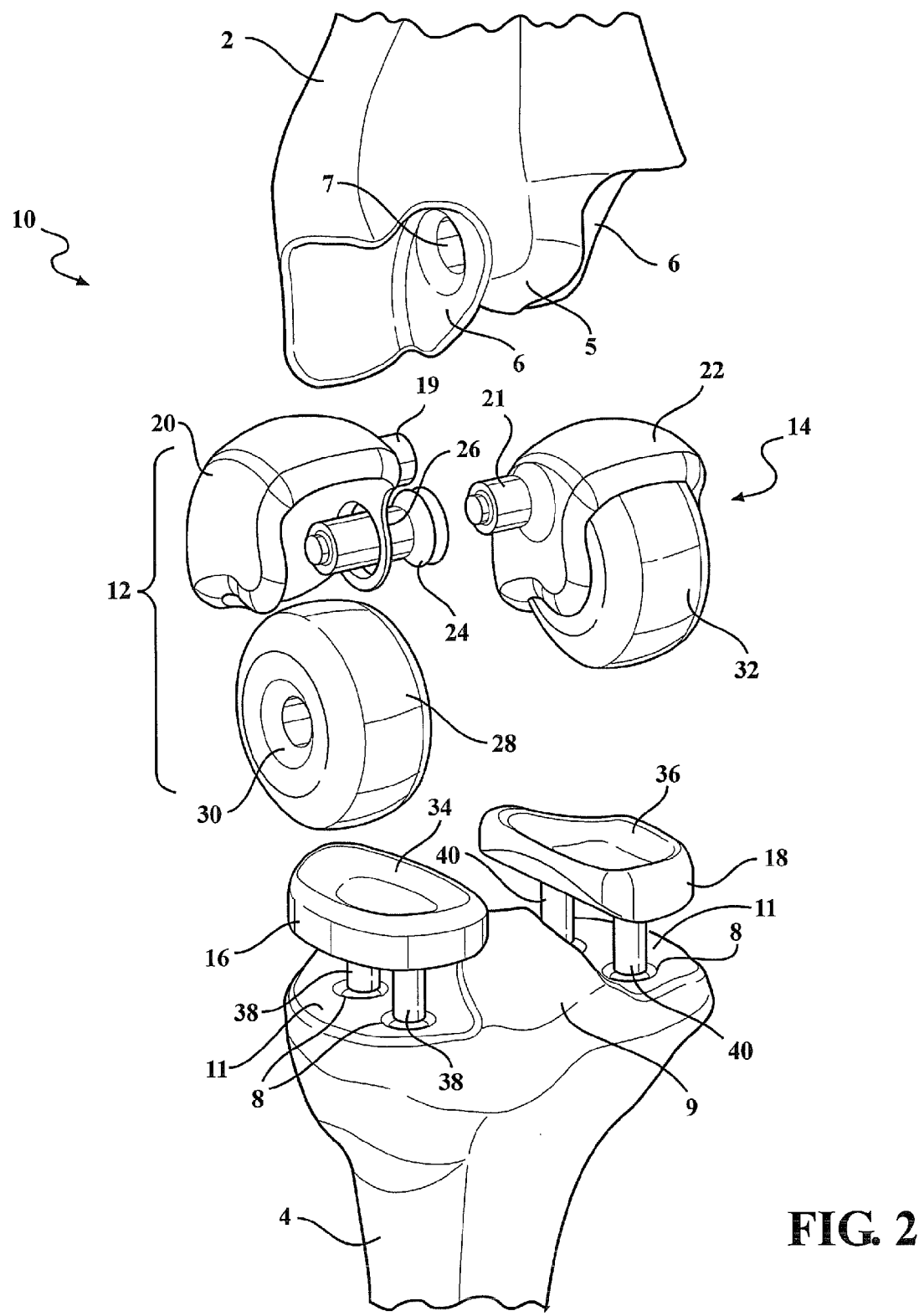
FIG. 2 is an exploded view of the multi-component assembly of FIG. 1 and better illustrating the reconditioned end-configurations established between the upper femur and lower tibia leg bones combined with the pairs of upper bone secured wheels and rotary support housings, combined with lower bone secured insert exhibiting upwardly facing support surfaces.

Referring to FIG. 1 again in collaboration with exploded view of FIG. 2, the joint assembly 10 better illustrates the reconditioned end-configurations, at 5 and 6 for femur 2, as well as at 8, 9 and 11 for tibia 4, these collectively supporting for implantation a first pair of upper bone secured wheel and rotary supporting well subassemblies, see as generally depicted at 12 and 14, combined with a further pair of lower bone secured inserts 16 and 18 exhibiting upwardly facing support surfaces. Each of the components 12-18 are constructed of any arrangement of metal, polymer, plastic, composite or other suitable material, with it further being understood that the individual pairs of components can be arrayed with any pattern of alternating materials. In this fashion, the desired wear properties and profiles are adjusted in part based upon the material selection of the individual components with concurrent objectives being both equalization of overall wear patterns established between the respective pairs of components and determining those situations in which metal on metal or plastic on plastic contact between the components is either desired or, more often, not.

Both the upper wheel and rotary supporting subassemblies 12 and 14 and lower bone secured inserts 16 and 18 are anchored in seating fashion within the inner recessed profiles 6 and 8 of the femur and tibia bones by use of a suitable medical cement (it further being understood that suitable bone adhesion can also be assisted or promoted by inner marrow in given circumstances). Upper wheel well housings 20 and 22 are associated with the subassemblies 12 and 14, each of which exhibits a three dimensional arcuate outer surface configured for seating within the reconditioned ends 6 of the upper femur 2, these further including lateral inward directed upper tabs 19 and 21 which seat within the laterally defined and recessed profiles 7 defined within the upper refashioned recess locations 6 in the femur 2.

As further depicted by selected well housing 20 shown in exploded fashion in FIG. 2, a laterally inserting and axially supporting pin 24 displaces relative to a circular lobe 26 associated with a side of the housing 20, this further defining a closed inner perimeter edge establishing the aperture for receiving the pin 24. An inner plastic wheel 28 is provided and includes a central axial through hole 30 which, upon pre-locating the wheel within the inner recess of the well housing 20, receives the inserting axial pin 24.

Although not shown, an extending end of the pin 24 seats within a journal end support at a hidden located on an inner face of the outer side of the housing (this to maintain the integrity of the shaft support). The width dimension of the wheel 28 (see also wheel 32 associated with corresponding well 22) can be dimensioned slightly less than the corresponding inner width dimension of the well housing recesses in order to facilitate a degree of lateral (side-to-side) motion of the wheels within the associated well housings in combination with rotary or spinning motion and upon assembly to replicate the subassembly further depicted at 14.

The lower bone secured inserts 16 and 18 each further exhibit surface exposed and slightly inwardly recessed surfaces or pockets, see as depicted at 34 and 36, for supporting in use the outer annular surfaces of the wheels 28 and 32 (see again FIG. 1). Inner (reverse side) pairs of extending stems 38 and 40 are provided for each of the inserts 16 and 18 and are recess mounting and cemented into place within the mating recess apertures 8 defined in the reconditioned end face of the lower tibia 4.

Figure 3:
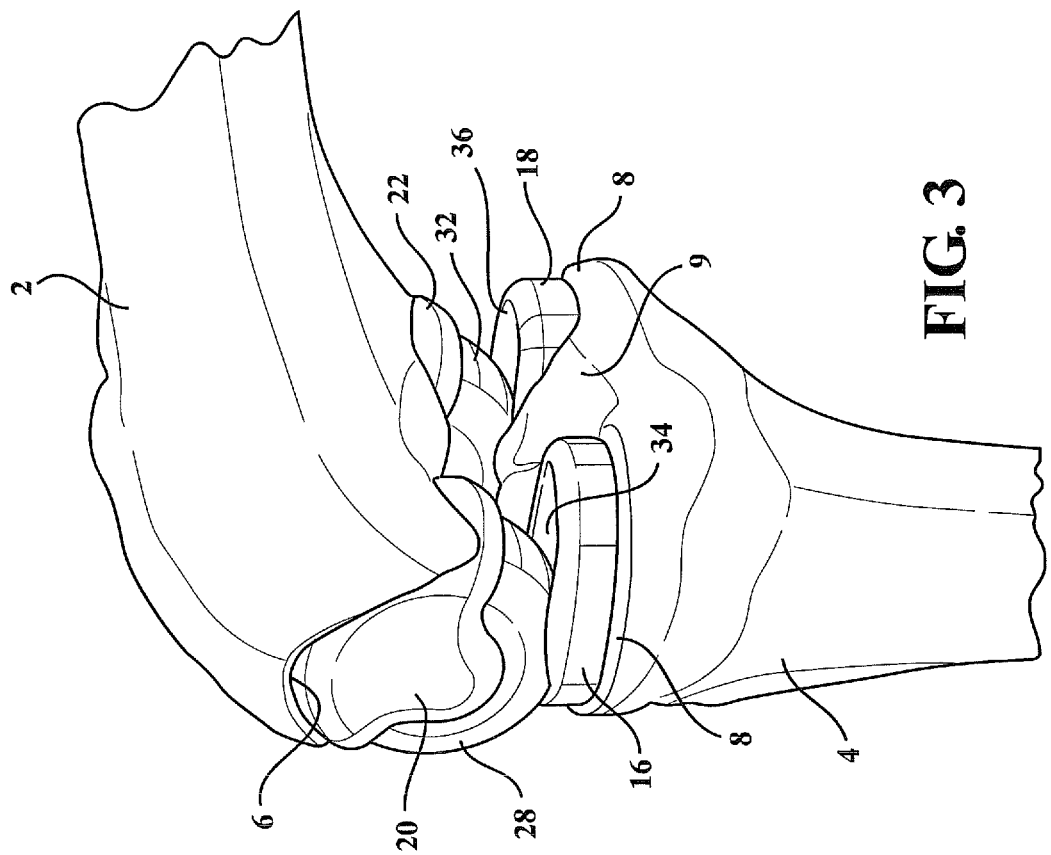
FIG. 3 is an assembled and substantially side rotated perspective similar to FIG. 1 and depicting a substantially 90° bend established between the upper femur and lower tibia with forward lineal displacement of the rotary supported wheels within the lower bone affixed and recessed pockets associated with the insert support.

FIG. 3 is an assembled and substantially side rotated perspective similar to FIG. 1 and depicts a substantially 90° bend established between the upper femur and lower tibia, with forward lineal displacement of the rotary supported wheels 28 and 32 within the lower bone affixed and slightly recessed pockets 34 and 36 associated with the lower affixed insert supports 16 and 18. In this fashion, FIG. 3 depicts a typical permitted range of pivotal motion afforded the joint assembly during use.

FIG. 4 is largely identical to FIG. 1 and presents only a selected side or ½ implant assembly according to a further potential sub-variant. The significance of FIG. 4 is to illustrate that sub-variants of the joint assembly can be incorporated into reduced of partial reconstructed applications, where applicable, and in situations where an entire reconstructed assembly is either unwarranted or unnecessary. Although not shown, the unreconstructed half of the joint assembly retains its original joint defining structure which, to the extent possible, is unaffected by the reconditioning performed to the implanted half of the joint assembly. Additionally, and although not further shown, any arrangement of natural or synthetically implanted ligament and tendon structure are also provided (or retained from the original pre-implantation reconditioning steps).

Figure 5:
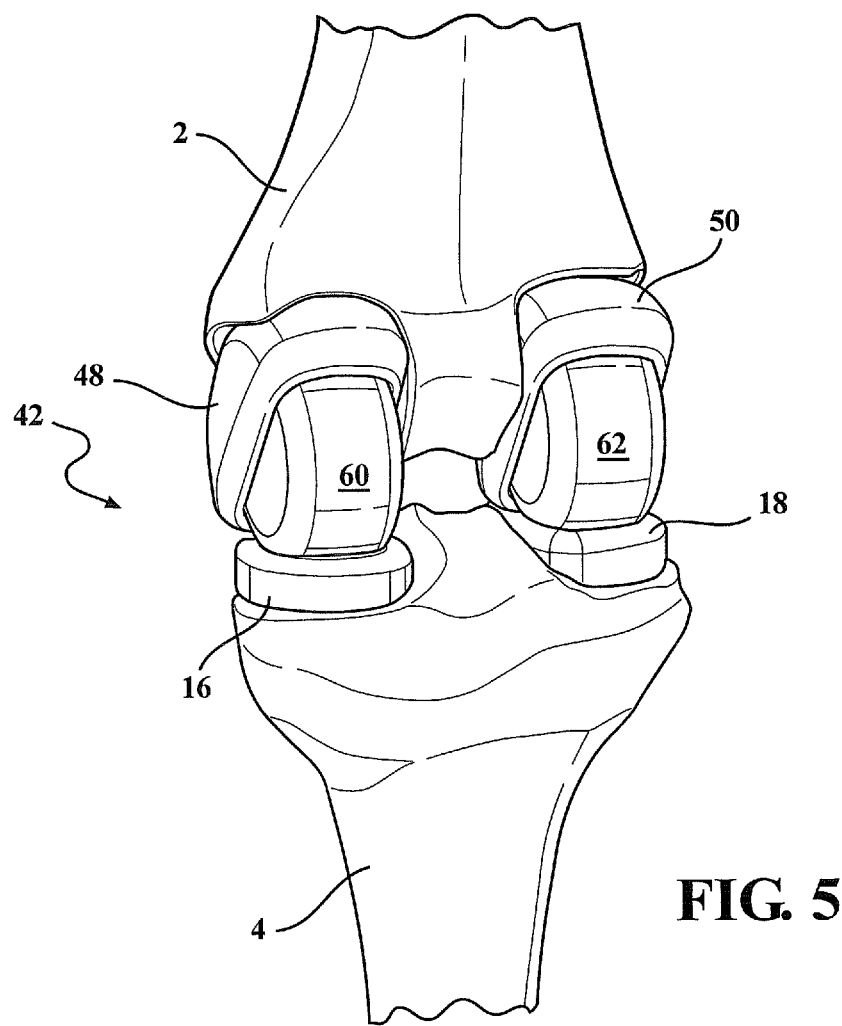
FIG. 5 is an illustration similar to FIG. 1 of a knee implant assembly according to a further preferred variant.
Figure 6:
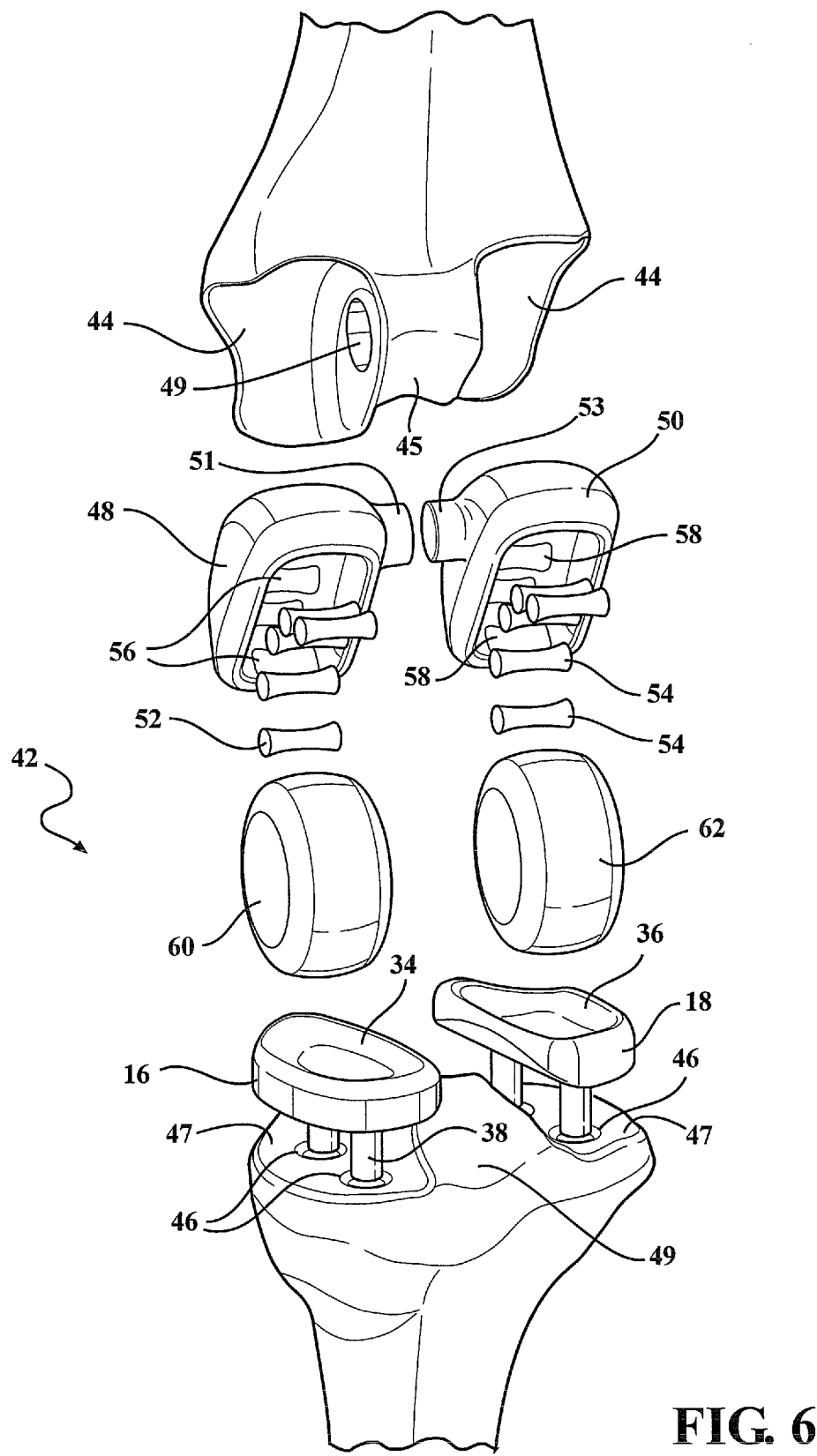
FIG. 6 is an exploded view of the multi-component assembly of FIG. 5 and better illustrating the reconditioned end-configurations established between the upper femur and lower tibia leg bones combined with a modified pair of upper secured wheel and rotary support housings exhibiting addition and inner well secured secondary bearings, combined with lower bone secure inserts exhibiting upwardly facing support surfaces.

Proceeding to FIGS. 5 and 6, a pair of perspective and exploded illustrations are depicted, in succession, of a knee implant assembly 42 similar to the variant previously described in FIG. 1 and according to a further preferred variant in which a different set of reconditioned and recess configured profiles within the joint defining end faces of the femur 2 and tibia 4 are defined. These include as respectively depicted at 44 for upper femur 2 with intermediate bridging surface 45, and further at 46 defined in conditioned ledge surfaces 47 with corresponding bridging surface 49, these in comparison to the configuration of the corresponding profiles 6 and 8 in FIG. 2.

As best depicted in the exploded view of FIG. 6, the upper profiles 44 again define a generally negative of an outer wheel well three dimensional profile for receiving associated outer three dimensional surfaces of a pair of outer wheel well housings 48 and 50 (these largely similar to those previously described at 20 and 22 in FIG. 2). Optionally, lateral pin seating recesses 49 can again be formed into the sides of the bridging location 45 defined in the reconditioned lower femur 2 and which can receive mating seating portions associated with the housings 48 and 50 (see for example as shown at 51 and 53) and so that the wheel wells 48 and 50 can be anchored into place in the manner shown in FIG. 5 through the use of a suitable medical bone adhesive or the like.

As further best shown in FIG. 6, the wheel housings 48 and 50 each exhibit additional and inner well secured secondary bearings (see as depicted by individual pluralities of elongated and width extending support bearings 52 and 54). These are in turn mounted within journaled interior recessed configured locations 56 and 58 defined in circumferentially spaced apart fashion around the interior of each of the inner wheel well housings 48 and 50 and so that, upon installing slightly modified plastic wheels 60 and 62, their outer annular surfaces are supported in roller bearing induced fashion by the circumferentially disposed bearing arrays 52 and 54 supported within the wheel well interiors in order to further facilitate ease of rotation of the wheels.

As with the previous embodiment, any type of journal supports can be incorporated into side locations of each wheel well housings 48 and 50 in order to retain in place the wheels 60 and 62 and which can again be dimensioned in order to establish any additional degree of side to side play or displacement in combination with its rotational aspects relative to the lower secured inserts. The lower bone secured inserts are again depicted at 16 and 18 as previously described in FIG. 2 for supporting annular locations of the wheels 60 and 2.

Figure 7:
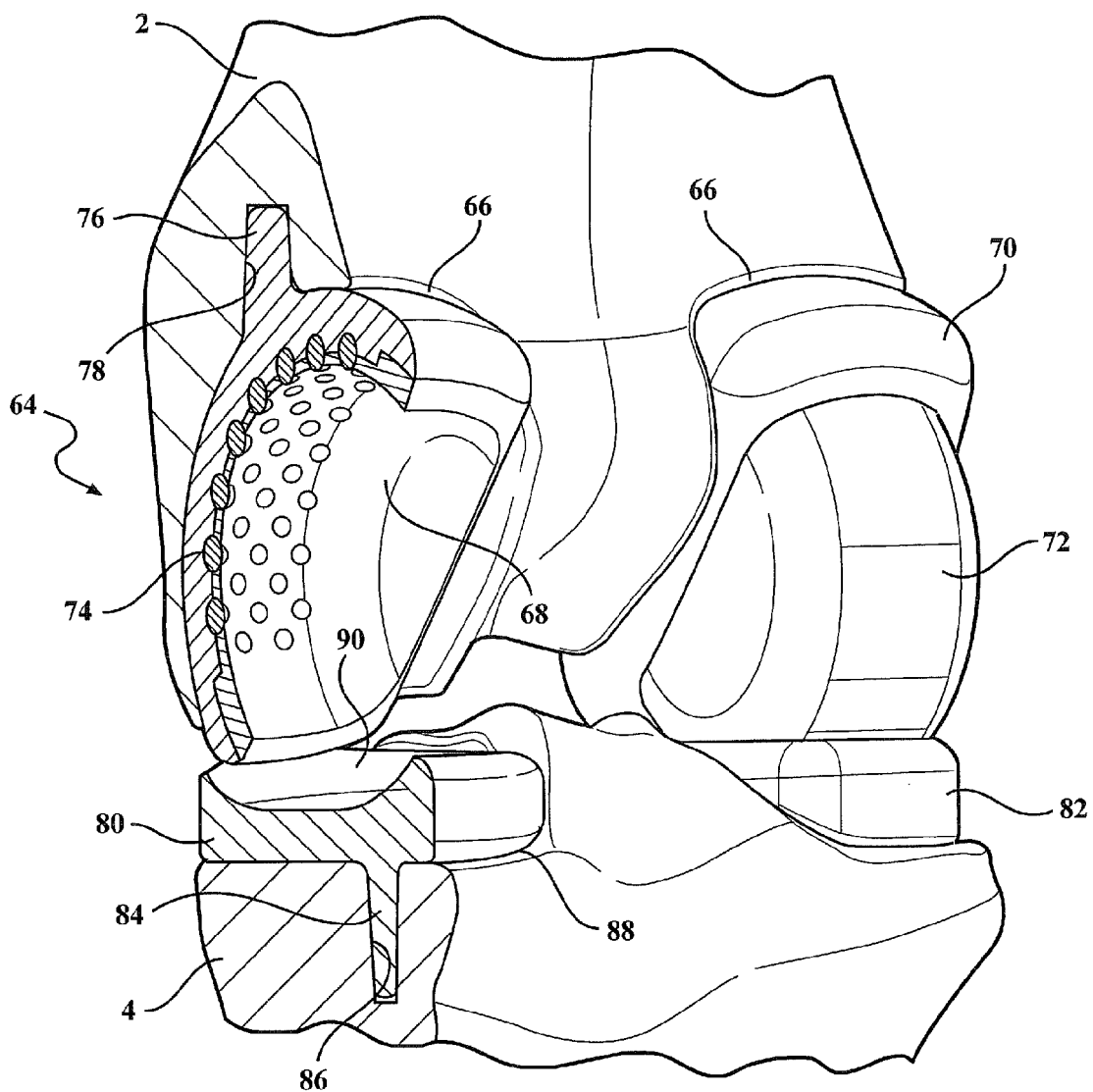
FIG. 7 is an enlarged perspective of a further knee implant assembly with a selected wheel well housing and associated bone surface shown in cutaway and with the associated rotary supported wheel removed in order to better illustrate a plural arrangement of substantially embedded and surface exposed eccentrically supporting ball bearings.

Finally, FIG. 7 is an enlarged perspective of a further knee implant assembly, generally at 64, with a selected wheel well housing and associated bone surface shown in cutaway (see refashioned upper femur end face profiles 66 with mounted upper wheel well housings 68 and 70. A wheel 72 is shown supported within selected housing 70, with corresponding wheel for cutaway housing 68 having been removed in order to better illustrate a plural arrangement of substantially embedded and surface exposed eccentrically supporting ball bearings 74.

As shown, the bearings 74 can be encapsulated into any type of material as previously described, and such that only arcuate tips thereof project from the inner exposed annular defined surfaces of the wheel well housing in a manner which contact the opposing exterior annular surfaces of the wheels in a similarly functional manner as described in reference to the width elongated bearings 52 and 54 of FIG. 6 (with the exception that the arrangement of FIG. 7 provides additional minor lateral displacement support to the wheel 72 depending upon the amount of play or movement associated with the supporting pin) and in order to provide both reinforced and easier rotational support to the wheels.

Similar to prior embodiments, the well housings 68 and 70 can each include an inner projecting stem location, see as shown by selected portion 76 in the cutaway of FIG. 7 associated with well housing 68 and which is received within an inner recessed aperture 78 associated with the overall reconditioned end face profile 66 defined of the upper femur 2, this again in order to better anchor and align into position the well housings 68 and 70 within the refashioned end configurations of the upper femur 2. Corresponding lower insert supports 80 and 82 are again provided in end anchored fashion within the refashioned lower end of the tibia 4. As depicted by sectional cutaway, a selected inner extending stem 84 is depicted in association with support 80 and is dimensioned so that it seats within an aligning pocket 86 defined within a refashioned or reconditioned ledge profile 88 of the tibia. Also depicted at 90 is the upwardly exposed and linearly supporting track profile (or pocket) revealed by the lengthwise cutaway of the selected insert support 80 and within which the wheels (such as at 72) are supported over their range of articulation.

Additional to the above described structural embodiments, additional aspects of the present inventions further contemplate a series of implantable joint assemblies which are incorporated into concurrently submitted shoulder and knee applications, with each exhibiting specific construction and functionality. Additional supporting descriptions pertaining to implantation procedures and considerations associated with such assemblies as described but not limited to the above are also presented as follows.

Application for Arthroplasty of the Shoulder
(Hemi-Arthroplasties, Tripolar, Replacement of)

An implantable device composed of metal, plastic, ceramic or composite materials used to replace a shoulder joint for fracture arthritis, degenerative disease or neoplasm which encompasses implants to the proximal humerus and glenoid that have a unique three piece construction and involves convex on concave articulating surfaces. The implants use an articulating central spherical component to act as a three piece articulating system, articulating between the glenoid component and the central spherical device as well as the articulation of the central spherical device onto the humeral implant.

The implant can also be designed as a two piece device using a spherical glenoid component, articulating with a head piece or modular humeral component which has concave or convex surfaces. The implantable interfaces may be amenable to polymethylmethacrylate or other adhesive or grout materials or may also be amenable to osteointegration surfaces.

Arthroplasty of the Shoulder Utilizing a Three Piece Device

The implants which may represent modular or non modular components as a portion of each of the implants. The implants would use a three piece configuration to allow degrees of constraint for an unstable shoulder or unstable primary or revision shoulder replacement. The implantable materials may be amenable to osteointegration or adhesive or grout devices to anchor the implants. The central spherical device would represent a three piece or tripolar design with elevated rims around the glenoid and humeral components to increase degrees of containment or constraint thus preventing dislocation or further instability of the implants.

The implants may be modular in nature to allow a modular humeral component as an alternative to a central and spherical free floating implant.

Application for Novel Design of Knee Arthroplasty

Development of an arthroplasty of the knee which replaces a single compartment, bicompartmental design or tricompartmental design of the knee utilizing a tripolar three piece design to provide minimal friction with articulation. The implant for the femoral implant would be of a concave capturing device, implantable in the femur with use of a fixation interface of either polymethylmethacrylate, grout or adhesive device or may be amenable to osteointegration. The tibial implant would be of a convex design, implantable to the upper tibia with either osteointegration, adhesives, grouts or polymethylmethacrylate type interfaces. The central, third piece would be a free floating articulation as a spherical implant to reduce friction and implant wear. I would recreate degrees of rotation, terminal lock, flexion and rotation through capturing minimal wear of implantable materials and increase longevity.

The implant would also involve designs for reciprocal concave and convex design to allow concave tibial implant capturing of a floating spherical tripolar third piece design inside of a concave femoral implant as degrees of constraint may be required in alternative anatomic situations.

A bicondylar design for a knee arthroplasty which would involve a three piece design, capturing separate condyle implants utilizing concave or convex surfaces on the femur or tibia, capturing a spherical third piece articulating implant which would allow degrees of constraint but also allow decreased wear on implantable materials. Implant interfaces could represent osteointegration surfaces or be amenable to polymethylmethacrylate, or adhesive or grout materials.

A single unit condylar design for unicompartmental arthroplasty of the knee, medial or lateral compartment which would allow a three piece design to be constrained or unconstrained implants amenable to convex or concave surfaces of the femur and the tibia which would capture a third piece spherical implant to reduce wear and improve range of motion and stability. The implant interfaces could be amenable to polymethylmethacrylate or osteointegration materials or other grout or adhesive materials.

A bicondylar or unicondylar design which would represent minimal bone resection of the femur and tibia which would allow a third spherical implant to be embedded into the femur or tibia to act as a three piece articulating design or tripolar design with implant interfaces amenable to osteointegration or adhesive or grout material such as polymethylmethacrylate. All implantable materials could represent metallic, ceramic or polyethylene or composite materials.

Application For Wear Debris Contained Total Knee or UKA

Design of unicondylar or bicondylar design for a knee arthroplasty utilizing a rubber bearing type design or other debris capturing design with contained bearing within the condyle of the femur or tibia to minimize wear debris and also collect wear debris to prevent dissemination of debris within the articular confines of a knee. The design would allow degrees of constraint as well as mobility with decreased component wear and collection of debris. Implants would be amenable to polymethylmethacrylate, adhesives, grouts or osteointegration to the fixation surfaces and could be constructed of metals, ceramics, plastics or polyethylenes or other component materials.

Application for Alternative Bearing Designed TKA

Development of a unicondylar or bicompartmental arthroplasty of the knee which would incorporate design to use a spherical roller bearing type wheel design which would allow reduced wear of component materials, improve mobility and stability of an implant or knee replacement. Design would allow either unicondylar replacement or bicompartmental replacement; fixation interfaces could be amenable to osteointegration, polymethylmethacrylate, or adhesive or grout materials. Designs could capture use of a wheeled design with axle in either a single condylar design or a bicompartmental design (such as referring to FIGS. 1 and 5).

Having described my invention, other and additional preferred embodiments will become apparent to those skilled in the art to which it pertains, and without deviating from the scope of the appended claims.

The invention claimed is:

1. A joint assembly incorporated into reconditioned end surfaces established between an upper bone and an opposing lower bone, said assembly comprising:

a pair of first components, each having an arcuate shaped body with an open bottom defining an interior accessible well housing, said first components adapted for being anchored into a pair of first reconditioned bone end surfaces associated with a selected one of the bones such that said first components are laterally spaced from each other, each of said first components receiving a rotatably supported wheel within said well housing; and a pair of second components adapted for being anchored into a second pair of reconditioned bone end surfaces associated with the other selected one of the bones such that said second components are laterally spaced from each other and in alignment with said first components, said second components each exhibiting an exposed support surface in contact with said rotatably supported wheel of a selected first component.

2. The joint assembly as described in claim 1, each of said first and second components further being constructed of at least one of a metal, plastic, polymer or composite material.

3. The joint assembly as described in claim 1, further comprising a laterally inserting and axially supporting pin displacing relative to a side of each of said interior accessible well housings, said wheels each including a central axial through hole which, upon pre-locating within the interior of said well, receiving a selected one of said pins in an inserting direction, an extending end of each of said pins seating within a journal end support defined on an opposing inner face of said well housing for supporting said shaft.

4. The joint assembly as described in claim 1, further comprising a width dimension of said wheel being dimensioned slightly less than a corresponding inner width dimension of said well housing in order to facilitate a degree of lateral (side-to-side) motion of said wheel in combination with rotational motion.

5. The joint assembly as described in claim 1, said well housings each further comprising additional and inner secured secondary width extending bearings mounted within journaled interior and circumferentially spaced locations such that contacting outer annular surfaces of said wheels are supported within said well housing interiors in order to further facilitate ease of rotation of said wheels.

6. The joint assembly as described in claim 1, said well housings each further comprising a plural arrangement of substantially embedded and surface exposed eccentrically supporting ball bearings within circumferentially defined locations such that contacting outer annular surfaces of said wheels are supported within said well housing interiors in order to further facilitate rotation of said wheels.

7. The joint assembly as described in claim 1, said exposed support surfaces of said pair of second components each further exhibiting a slightly inwardly recessed profile for supporting an outer annular surfaces of said wheel, a reverse underside of said second component further including an integrally extending stem recess mounting within the second reconditioned bone end surfaces.

\* \* \* \* \*